United States Patent
Fuhrman et al.

(10) Patent No.: US 8,602,026 B2
(45) Date of Patent: Dec. 10, 2013

(54) BREATHING-GAS DELIVERY AND SHARING SYSTEM AND METHOD

(75) Inventors: Bradley P. Fuhrman, Buffalo, NY (US); Mark S. Dowhy, West Seneca, NY (US)

(73) Assignee: The Research Foundation of State University of New York, Amherst, NY (US)

( * ) Notice: Subject to any disclaimer, the term of this patent is extended or adjusted under 35 U.S.C. 154(b) by 1158 days.

(21) Appl. No.: 12/197,147

(22) Filed: Aug. 22, 2008

(65) Prior Publication Data

US 2009/0050151 A1 Feb. 26, 2009

Related U.S. Application Data

(60) Provisional application No. 60/957,383, filed on Aug. 22, 2007, provisional application No. 61/014,312, filed on Dec. 17, 2007.

(51) Int. Cl.
*F16K 31/02* (2006.01)

(52) U.S. Cl.
USPC ............. 128/204.21; 128/204.23; 128/204.26

(58) Field of Classification Search
USPC ............. 128/200.24, 204.18, 204.21, 204.23, 128/204.26, 205.11, 203.12, 203.15, 128/203.16, 203.25, 203.26, 203.27
See application file for complete search history.

(56) References Cited

U.S. PATENT DOCUMENTS

| | | | | |
|---|---|---|---|---|
| 4,520,808 A * | 6/1985 | LaBauve | ................. | 128/200.14 |
| 4,721,060 A * | 1/1988 | Cannon et al. | ................. | 119/420 |
| 4,883,051 A * | 11/1989 | Westenskow et al. | ... | 128/204.21 |
| 5,297,502 A * | 3/1994 | Jaeger | ........................ | 119/420 |
| 5,664,563 A | 9/1997 | Schroeder et al. | | |
| 6,095,138 A * | 8/2000 | Hognelid et al. | ........ | 128/204.18 |
| 6,105,582 A | 8/2000 | Pranevicius et al. | | |
| 6,158,430 A * | 12/2000 | Pfeiffer et al. | ........... | 128/202.27 |

(Continued)

FOREIGN PATENT DOCUMENTS

| | | |
|---|---|---|
| JP | 2002-272848 | 9/2002 |
| JP | 2006-527635 A | 12/2006 |
| WO | 2005/000805 A2 | 1/2005 |

OTHER PUBLICATIONS

Neyman et al.; A Single Ventilator for Multiple Simulated Patients to Meet Disaster Surge; Academic Emergency Medicine, Nov. 2006, vol. 13, No. 11; pp. 1246-1249.

*Primary Examiner* — Glenn Richman
(74) *Attorney, Agent, or Firm* — Hodgson Russ LLP

(57) ABSTRACT

A device, system, and method for isolating a ventilator from one or more patients in which the delivery conditions of gas delivered to an isolation device from a ventilator may drive the delivery of breathing-gas delivered to one or more patients, the breathing-gas having the same or different delivery conditions. In one embodiment, an isolation device may have a housing and a movable partition. The movable partition may be joined to the housing, The movable partition may have a patient side on a first side of the partition and an actuating side on a second side of the partition. The isolation device may include an inlet pressure regulator on the actuating side and/or an exhaust pressure regulator on the patient side. These regulators may alter the delivery conditions (including, but not limited to, pressure and volume) of breathing-gas delivered to a patient.

20 Claims, 12 Drawing Sheets

(56) References Cited

U.S. PATENT DOCUMENTS

| | | | |
|---|---|---|---|
| 6,776,158 B1 * | 8/2004 | Anderson et al. | 128/203.12 |
| 7,721,736 B2 * | 5/2010 | Urias et al. | 128/204.23 |
| 8,225,788 B2 * | 7/2012 | Manigel et al. | 128/204.21 |
| 2003/0015199 A1 | 1/2003 | Fuhrman et al. | |
| 2004/0035424 A1 * | 2/2004 | Wiesmann et al. | 128/204.26 |
| 2005/0040646 A1 | 2/2005 | Brumfield et al. | |
| 2006/0189880 A1 | 8/2006 | Lynn et al. | |
| 2007/0021795 A1 | 1/2007 | Tehrani | |

* cited by examiner

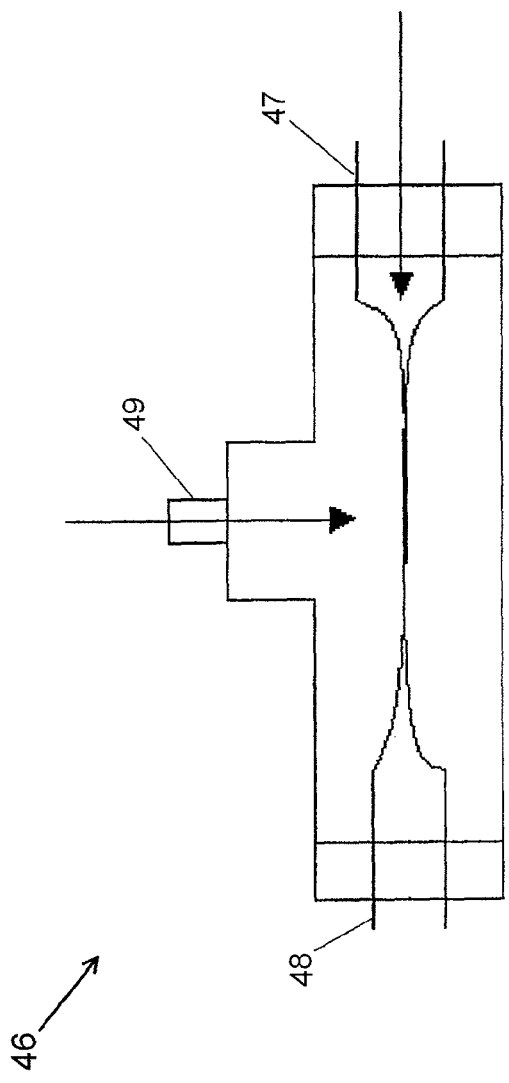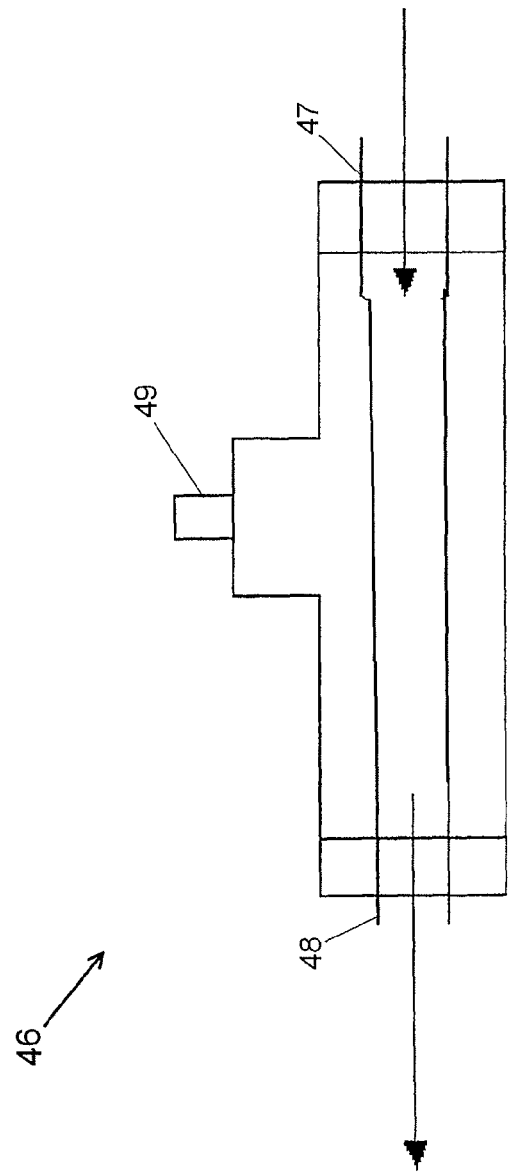
FIG. 7A
FIG. 7B

BREATHING-GAS DELIVERY AND SHARING SYSTEM AND METHOD

CROSS-REFERENCE TO RELATED APPLICATION

This application claims the benefit of priority to U.S. provisional patent application Ser. No. 60/957,383, filed on Aug. 22, 2007 and 61/014,312, filed on Dec. 17, 2007, the disclosures of which are incorporated herein by reference.

FIELD OF THE INVENTION

The present invention relates to patient ventilators. The present invention may include one or more isolation devices associated with a patient ventilator, and these may be used to provide breathing-gas to one or more patients.

BACKGROUND OF THE INVENTION

The term "ventilator" is used herein to refer collectively to respirators and ventilators, including various high frequency ventilators. In a hospital, patients may need the assistance of a ventilator when they cannot breathe on their own. Ventilators are expensive machines, and consequently hospitals tend not to have a large number of excess ventilators. Pandemics are relatively infrequent, but potentially devastating mass casualty events. There have been three influenza pandemics in the past century, and an estimated 32 in the past 400 years. In the event of a pandemic, such as that which might be caused by a mutant form of Influenza H5N1, which is already endemic in wild birds and domestic fowl throughout Asia, the number of patients that need ventilators may exceed the available supply. Estimates of the magnitude of the shortage indicate that from 30% to 200% more ventilators will be needed in a pandemic situation. During such a shortage, physicians may be faced with the unpleasant decision of terminating the use of a ventilator by one patient so that another patient may use it, or of withholding ventilator support from a new patient in need. In some situations, terminating or failing to provide the use of a ventilator, even temporarily, will result in a prolonged recovery time for a patient, harm to the patient, or even loss of the patient's life.

A single ventilator can be used to support several patients simultaneously, thereby increasing the number of patients who can be treated, but existing technology does not prevent cross contamination. That is to say that when patients share a ventilator using existing technology, the diseases, bacteria and viruses, carried by one patient may contaminate the environment and equipment used by another patient, and may be directly transmitted to the other patient. Furthermore, existing technology for sharing a ventilator severely limits the capacity to accommodate each individual patient's separate respiratory support needs because no mechanism is provided to separately accommodate each patient's respiratory needs, such as, for example, individualized tidal volume, peak pressure, oxygen concentration, and positive end-expiratory pressure ("PEEP").

There has been no prior description of the use of a re-breathing circuit to allow aseptic sharing of a ventilator among two or more patients. U.S. Pat. No. 6,675,799 (the "'799 Patent") describes a re-breathing device that was intended to isolate a single patient from his/her ventilator, caregivers, and environment. However, the '799 Patent does not disclose how to ventilate more than one patient at the same time using a single ventilator. Nor does the '799 Patent address: (1) how to reduce patient tidal volume below the volume delivered to the device by a shared ventilator; (2) how to limit peak airway pressure below that set on the shared ventilator, (3) how to individualize oxygen concentration of patients sharing a ventilator; (4) how to increase PEEP above that set by a shared ventilator; or (5) how to conserve oxygen when several patients share a ventilator, all of which may be essential to the individualization of patient settings during shared ventilation. By way of contrast, an isolation device according to the present invention has the ability to alter the delivery conditions of breathing-gas and thereby individualize the characteristics of the breathing-gas patients receive using a ventilator that may be shared among several patients. This capability to alter the conditions under which breathing-gas may be provided to a patient using a disposable device, allows an inexpensive ventilator, having little sophistication, to deliver breathing-gas having better defined pressure, volume, and oxygen concentration characteristics to a patient.

Additionally, ventilators operate by using a supply of compressed gas to mechanically ventilate the lungs of a patient by increasing the pressure in the patient's airway. Typically, a ventilator requires both compressed air and compressed oxygen, in varying ratios depending on a patient's needs. Less-expensive ventilators, like those stockpiled for pandemic preparedness, may not make efficient use of the gases supplied. This inefficiency is inconsequential with regard to compressed air because, in hospitals, mechanical compressors can be used to generate a continuous supply of pressurized air on-site, so shortages of compressed air are not anticipated, even during a pandemic. Compressed oxygen, however, is usually generated by gas suppliers located off-site and is generally provided to hospitals as compressed oxygen in tanks, or as liquid oxygen. In a pandemic, shortages of both compressed and liquid oxygen are anticipated. Oxygen concentrators can be used to generate oxygen for spontaneously breathing patients, but cannot be used with most ventilators since most ventilators require a pressurized gas inflow at a pressure higher than can be generated by a typical oxygen concentrator. It would therefore be advantageous to have a system, which reduces the amount of oxygen required for mechanical ventilation by using only compressed air to power lung inflation and an efficient re-breathing device to provide oxygen to the patient. No means has previously been described to conserve available oxygen when using less-expensive ventilators to cope with the expected shortage of pressurized oxygen or during a shortage of more advanced ventilators. The use of a re-breathing device to conserve oxygen would help meet these needs.

During a mass casualty event, deploying disposable isolation devices to conserve oxygen and convert inexpensive, unsophisticated, oxygen-wasteful ventilators into affordable, yet more sophisticated, oxygen conserving, isolating ventilators, could save lives. This is not foreseen by the '799 Patent.

SUMMARY OF THE INVENTION

The invention may be embodied as a device for isolating a ventilator from one or more patients. Such a device may have a housing and a movable partition. The movable partition may be joined to the housing and have a patient side of the partition and an actuating side of the partition. A ventilator may be connected to the housing on the actuating side of the partition so that the ventilator is able to move the partition. The isolation device may include an inlet pressure regulator on the actuating side and/or an exhaust pressure regulator on the patient side. These regulators may alter the delivery conditions (including, but not limited to, pressure and volume) of breathing-gas delivered to a patient.

The invention may be embodied as a system which includes a ventilator and two or more isolation devices, which may be similar to that described above. Such a system may be used to provide breathing-gas to more than one patient using a ventilator. In a system of this embodiment, inlet pressure regulators and/or exhaust pressure regulators may be used to individualize delivery conditions of the breathing-gas delivered to each patient according to his or her needs.

The invention may be embodied as a method for using a ventilator to provide breathing-gas to at least two patients by way of a ventilator and at least two isolation devices. The isolation devices may be similar to those described above, and may include inlet and/or exhaust pressure regulators to individualize the delivery conditions of the breathing-gas delivered to each patient according to his or her needs.

The invention may be embodied as a method for enhancing the performance of a ventilator. A method of this embodiment may use a ventilator and an isolation device similar to that described above, which includes an inlet pressure regulator and/or an exhaust pressure regulator to modify the delivery conditions of breathing-gas delivered to a patient.

BRIEF DESCRIPTION OF THE DRAWINGS

For a fuller understanding of the nature and objects of the invention, reference should be made to the accompanying drawings and the subsequent description. Briefly, the drawings are:

FIG. 7A is a diagram of a Starling resistor shown in a closed (occluded) configuration;

FIG. 7B is a diagram of a Starling resistor shown in an open configuration;

FURTHER DESCRIPTION OF THE INVENTION

Figure 1:
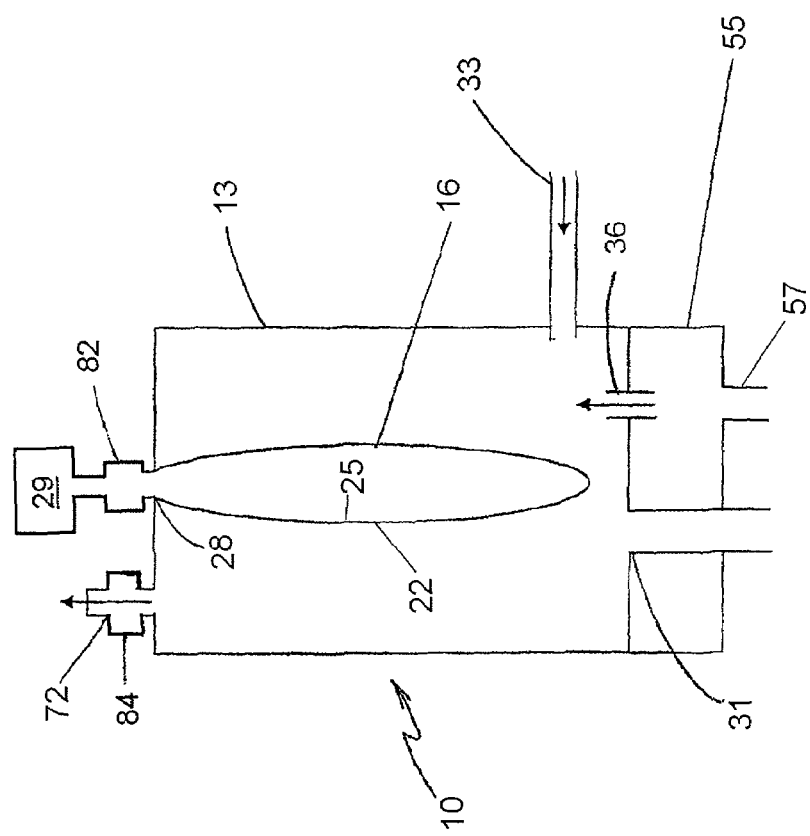
FIG. 1 is a diagram of a device according the invention.

The invention may be embodied as a device for isolating a ventilator from one or more patients. FIG. 1 shows an isolation device 10 according to the present invention. The isolation device 10 may have a housing 13 disposed about a movable partition 16. The movable partition 16 may be joined to the housing 13 and have a patient side 22 of the movable partition 16 and an actuating side 25 of the movable partition 16. The movable partition 16 may be in the form of a flexible bag. The isolation device 10 may include an inlet pressure regulator 82 in fluid communication with the actuating side 25. The inlet pressure regulator 82 may regulate the pressure of breathing-gas allowed on the actuating side 25. The inlet pressure regulator 82 may also limit the pressure on the actuating side 25 to a desired maximum ("peak pressure"). The isolation device 10 may include an exhaust pressure regulator 84 in fluid communication with the patient side 22 of the movable partition 16. The exhaust pressure regulator 84 may regulate a pressure in the housing 13 on the patient side 22 during exhalation and may be used to generate a PEEP on the patient side 22 that differs from that of a ventilator by, for example, restricting the outflow of gas from the housing 13 on the patient side 22, thus maintaining a higher end-expiratory pressure than may be set on a ventilator.

Figure 4:
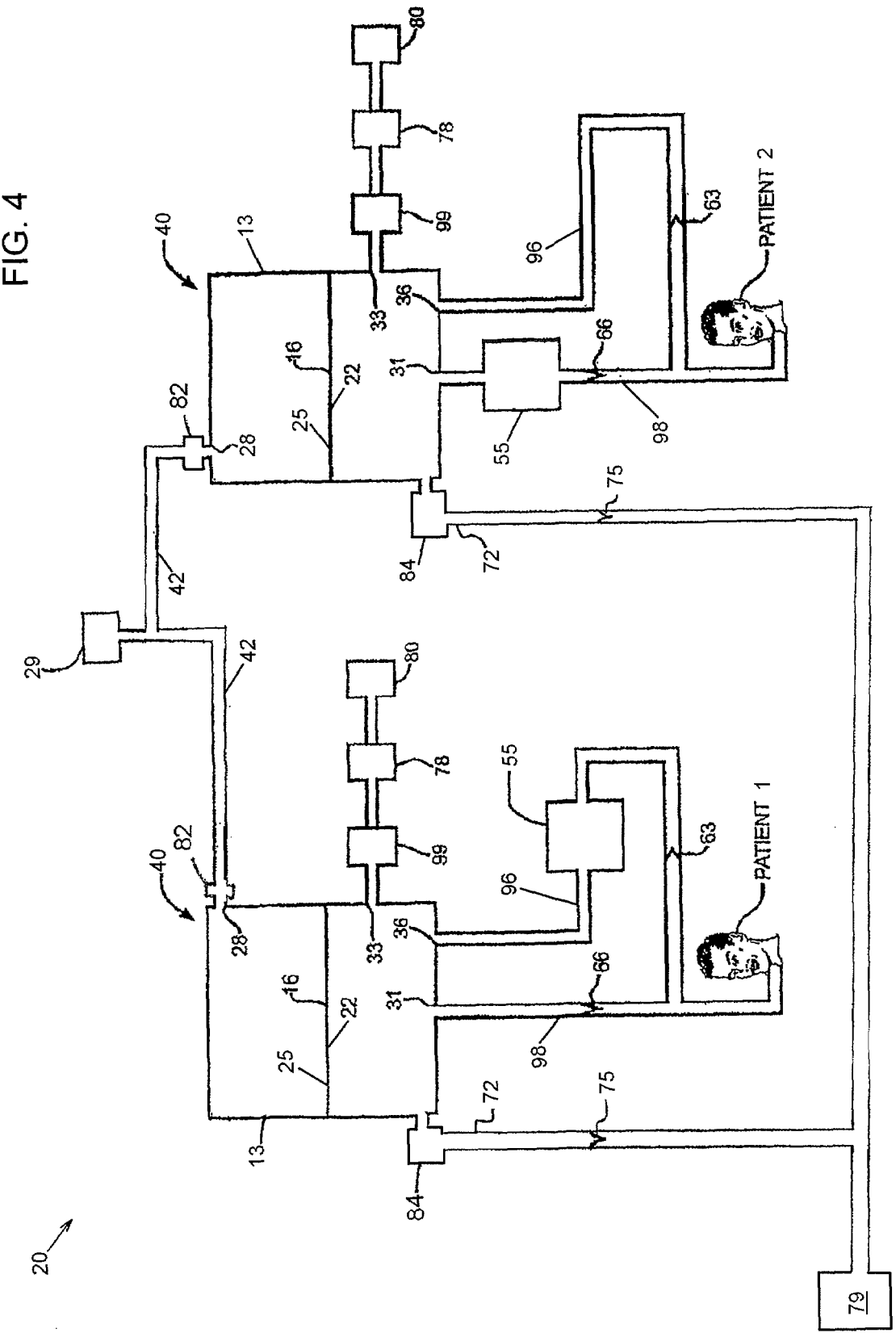
FIG. 4 is a schematic showing details of the embodiment of FIG. 2.

The housing 13 also may have a ventilator orifice 28 in fluid communication with the actuating side 25 that is adaptable to be in pneumatic communication with a ventilator 29. The housing 13 also may have a patient inspiration orifice 31 in fluid communication with the patient side 22 that is adaptable to be in pneumatic communication with a patient. The housing 13 may have a bias inflow orifice 33 in fluid communication with the patient side 22 that is adaptable to be in pneumatic communication with a source of fresh inspiratory gas 80. The housing 13 may have an expiration return orifice 36 in fluid communication with the patient side 22. The isolation device 10 may also include a $CO_2$ scrubber 55 in fluid communication with the patient side 22 to reduce the level of $CO_2$ in the gas that returns to the patient during re-breathing. Such a scrubber 55 may be located so that breathing-gas from the housing 13 flows through the scrubber 55 to the patient on inspiration, and/or so that breathing-gas from the patient flows through the scrubber 55 to the housing 13 on expiration. FIG. 4 depicts a scrubber 55 connected to "Patient 1" by way of an exhalation line 96 and another scrubber 55 connected to "Patient 2" by way of an inhalation line 98.

Figure 2:
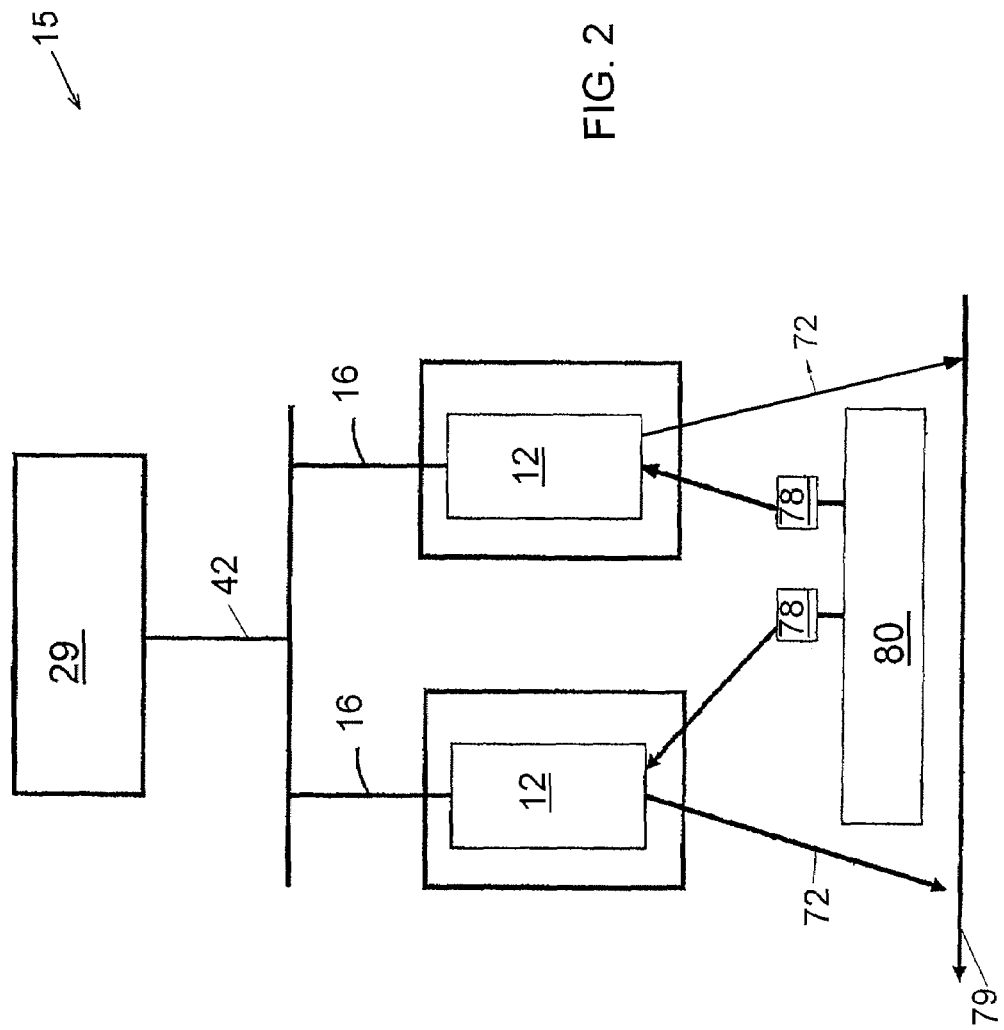
FIG. 2 is a schematic of a system according to an embodiment of the invention.
Figure 3:
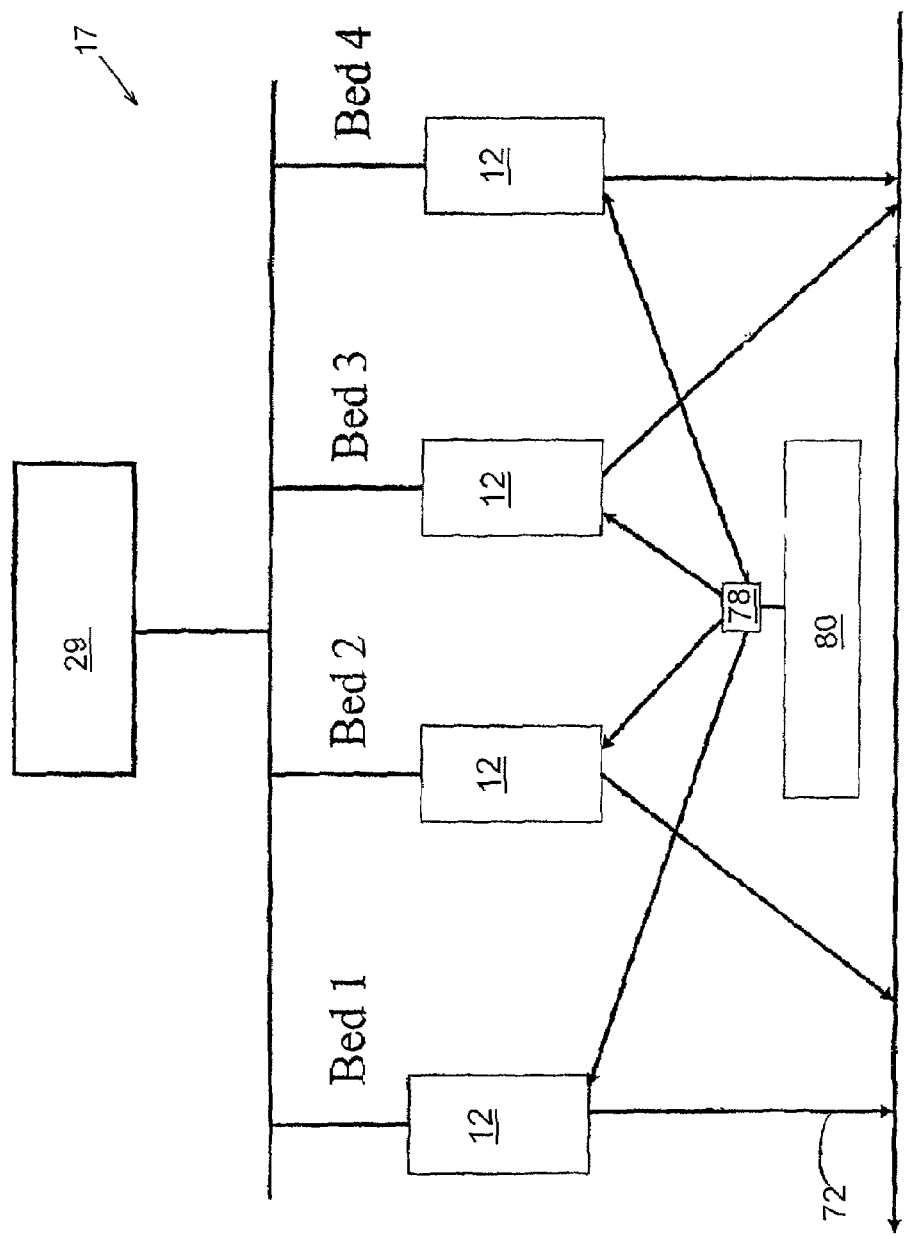
FIG. 3 is a schematic showing a system according to another embodiment of the invention.

FIG. 2 shows that the invention may be embodied also as a breathing-gas sharing system 15. In such a system 15, a ventilator 29 and at least two isolation devices 12 are provided. The ventilator 29 may be connected to an inlet 16 of each of the isolation devices 12 by way of ventilation path 42. The isolation devices 12 may be of many types known in the art, for example, the type disclosed in the '799 patent, or the type described above. FIG. 3 schematically depicts another embodiment of a breathing-gas sharing system 17 in which four isolation devices 12 are shown. One patient could be associated with each isolation device 12.

FIG. 4 depicts a breathing-gas delivery system 20 according to another embodiment of the invention. The system 20 of this figure is shown with two patients being ventilated by a single ventilator 29, and using two isolation devices 40 that function like that described above. Each housing 13 may be made of more than one piece, for example, the portion of the housing 13 on the patient side 22 may be one piece and the portion on the actuating side 25 may be another piece. The portion of the housing 13 on the patient side 22 may receive fresh gas from a fresh gas source 80. The fresh gas flow may be controlled by a fresh gas controller 78 and the fresh gas may be altered by a conditioner 99. The conditioner 99 may be, for example, a vaporizer, a nebulizer, a blender, a mixer, a humidifier, or any combination of these devices. FIG. 4 shows that patients may be connected to re-breathing circuits, and that the re-breathing circuits may include check valves 66, 63 and a $CO_2$ scrubber 55.

In operation, the ventilator 29 may be set to provide either: (1) a peak pressure and a desired end-expiratory pressure (the "pressure-mode"); or (2) a desired tidal volume and end-expiratory pressure (the "volume-mode"). In pressure-mode operation, the isolation device 40 may be provided with the peak pressure and the end-expiratory pressure of the ventilator 29, and a patient will get a tidal volume determined by their chest compliance. If more than one isolation device 40 (and therefore more than one patient) is connected to the ventilator 29 in pressure-mode, then any particular patient will receive a tidal volume determined by that patient's chest compliance. However, in such a case, the tidal volume delivered to a patient may not be appropriate for that patient; for example, the peak pressure may cause a tidal volume that is too low for a particular patient, thus not delivering enough oxygen to, or removing enough carbon dioxide from, that patient. In order to avoid that situation, the peak pressure may be selected so as to adequately ventilate the stiffest lung among those that are being ventilated, provided that the peak pressure does not exceed some safe upper limit (e.g. 35 to 50 cm of water).

Figure 5:
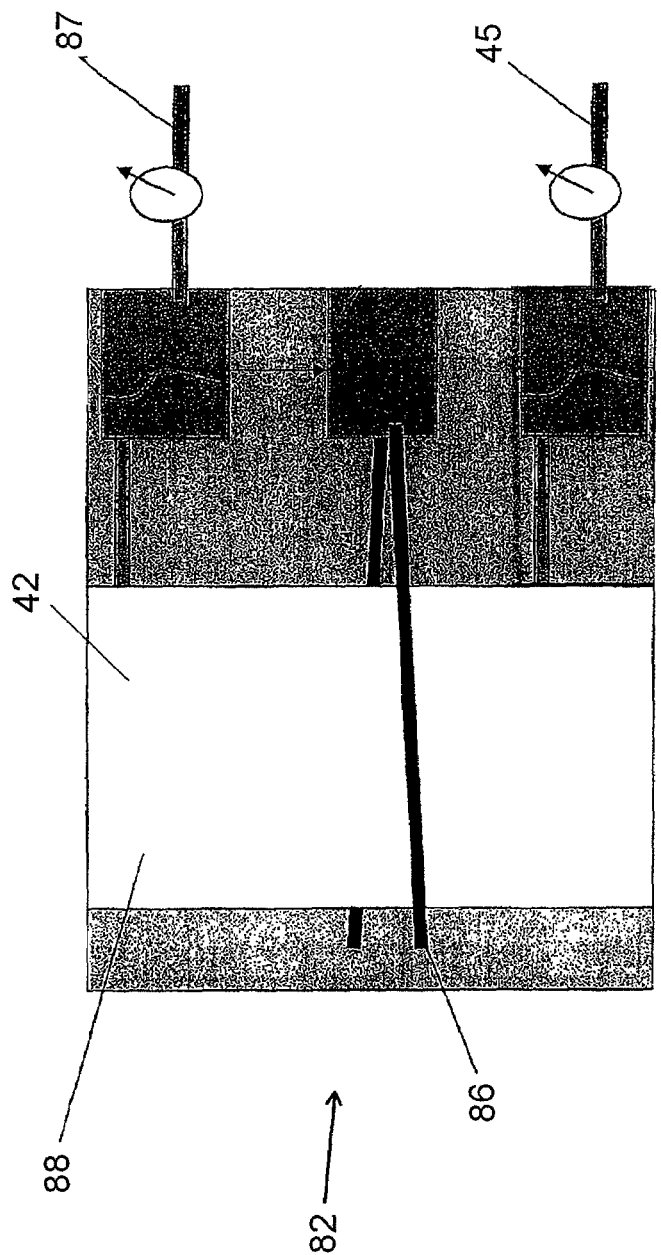
FIG. 5 is a diagram of one type of inlet pressure regulator.

The peak pressure delivered to a particular isolation device 10 may be reduced below the ventilator 29 peak pressure using an inlet pressure regulator 82 (FIG. 1), which may partially or completely occlude the ventilation path 42, which connects the ventilator 29 to the isolation device 10. FIG. 5 depicts one such inlet pressure regulator 82 that uses a ventilator path occlusion caliper 86 to work against a flexible tube 88. An adjustable signal may be provided to the inlet pressure regulator 82 by, for example, a pressure transducer 87. Re-opening of this inlet pressure regulator 82 may be initiated by a subsequent signal, in response to, for instance, a fall in ventilator 29 pressure below that of the isolation device 10, which may be measured by, for example, a downstream pressure transducer 45. Such a fall in ventilator 29 pressure (below that of the isolation device 40) may occur at the onset of a pre-set ventilator 29 expiratory cycle if the inlet pressure regulator 82 has closed the tube 88.

In a system 20 of the present invention, the ventilator 29 may serve as a timing device to set the respiratory cycle and power the mechanical ventilation of the lungs of one or more patients via the isolation device(s) 40. For this reason, the ventilator 29 need not be an expensive, advanced device since the isolation device 40 may control patient-specific parameters such as, for example, patient tidal volume, peak airway pressure, and PEEP. Therefore, it should be understood that the ventilator 29 may be, among other things, a mechanical ventilator, a manual ventilator such as an ambu bag, or a continuous positive airway pressure ("CPAP") device which merely delivers constant positive airway pressure.

Ventilators 29, especially less expensive models, may use large volumes of gas to perform the ventilation function. Further, these devices may be "leaky" in that some of the gas provided to the ventilator may be lost due to leaks or other inefficiencies and therefore, not fully delivered to the patient. When ventilators are supplied with gas supplemented by oxygen, the leaks may cause an inefficient use of this supplemental oxygen—a resource which may be in short supply. In a system 20 of the present invention, the ventilator 29 may use room air from a compressor to move the partition 16 in the isolation device(s) 40. This may alleviate the need to supply the potentially inefficient ventilator 29 with both pressurized air and pressurized oxygen as would be required when using a ventilator 29 to directly ventilate a patient without the use of isolation device(s) 40. When using pressurized air in the ventilator 29 to move partition 16 in the isolation device(s) 40, each patient's oxygen needs may be met by providing supplemental oxygen directly to each isolation device 40 where the oxygen may be more efficiently used. The fresh gas source 80 may include a system to supply oxygen from a liquid oxygen tank, compressed gas cylinder, or oxygen concentrator. Fresh gas flow rates may be selected independently for each isolation device 40. The fresh gas flow rates may be selected to complete filling of the lungs to an optimal peak pressure with the ventilator path occlusion caliper 86 closed. In order to do so, the occlusion caliper 86 may remain open while the ventilator 29 may be used to deliver inhalation gas to the patient, and when the ventilator 29 has reached a predetermined pressure, for example its peak pressure, the occlusion caliper 86 may be closed and fresh gas flow may, then, be used to augment tidal volume above that propelled by the ventilator 29.

A conditioner 99, may be, for example, a blender to mix oxygen and air to individualize oxygen concentration of the gas supplied to the portion of the isolation device 40 on the patient side 22. A re-breathing circuit may be employed to more completely utilize the fresh gas entering the portion of the isolation device 40 on the patient side 22. Using a re-breathing circuit, the system 20 may use low fresh gas flow rates, and that may reduce the use of oxygen to a fraction of what would otherwise be required.

To control the end-expiratory pressure, the signal to the inlet pressure regulator 82 may also be used to control an exhaust pressure regulator 84 (see FIGS. 1 and 6) to occlude a gas exhaust line 72 (see FIGS. 1 and 2) and to prevent exhausting gas from the portion of the isolation device 10, 40 on the patient side 22 during inspiration. Alternatively, a Starling resistor may be used to regulate the release of gas from the portion of the isolation device 10, 40 on the patient side 22 and such a Starling resistor may be connected such that pressure within the isolation device 10, 40 must exceed the pressure in the ventilator circuit in order for exhaust to leave the portion of the isolation device 10, 40 on the patient side 22. FIGS. 7A and 7B depict such a Starling resistor 46—in the closed and open configuration, respectively—wherein a gas flow from a resistor inlet 47 to a resistor outlet 48 is controlled by the pressure in a control line 49. In use, the resistor inlet 47 of the Starling resistor 46 may be connected to the portion of the isolation device 10, 40 on the patient side 22, the resistor outlet 48 may be connected to the gas exhaust line 72, and the control line 49 may be connected to the ventilator path 42, between the housing 13 and the inlet pressure regulator 82. A manually adjustable PEEP valve 89, located either before or after the Starling resistor or caliper, may then be used to up-regulate PEEP above that set on the ventilator 29 when it is necessary to modify the patient's PEEP to exceed that set by the ventilator 29. This may have the additional benefit of promoting the emptying of the portion of the isolation device 10, 40 on the actuating side 25 before the next inhalation, assuring consistency of delivered tidal volume. In an alternative embodiment shown in FIG. 10, the PEEP valve may be located in the ventilator path 42.

Figure 6:
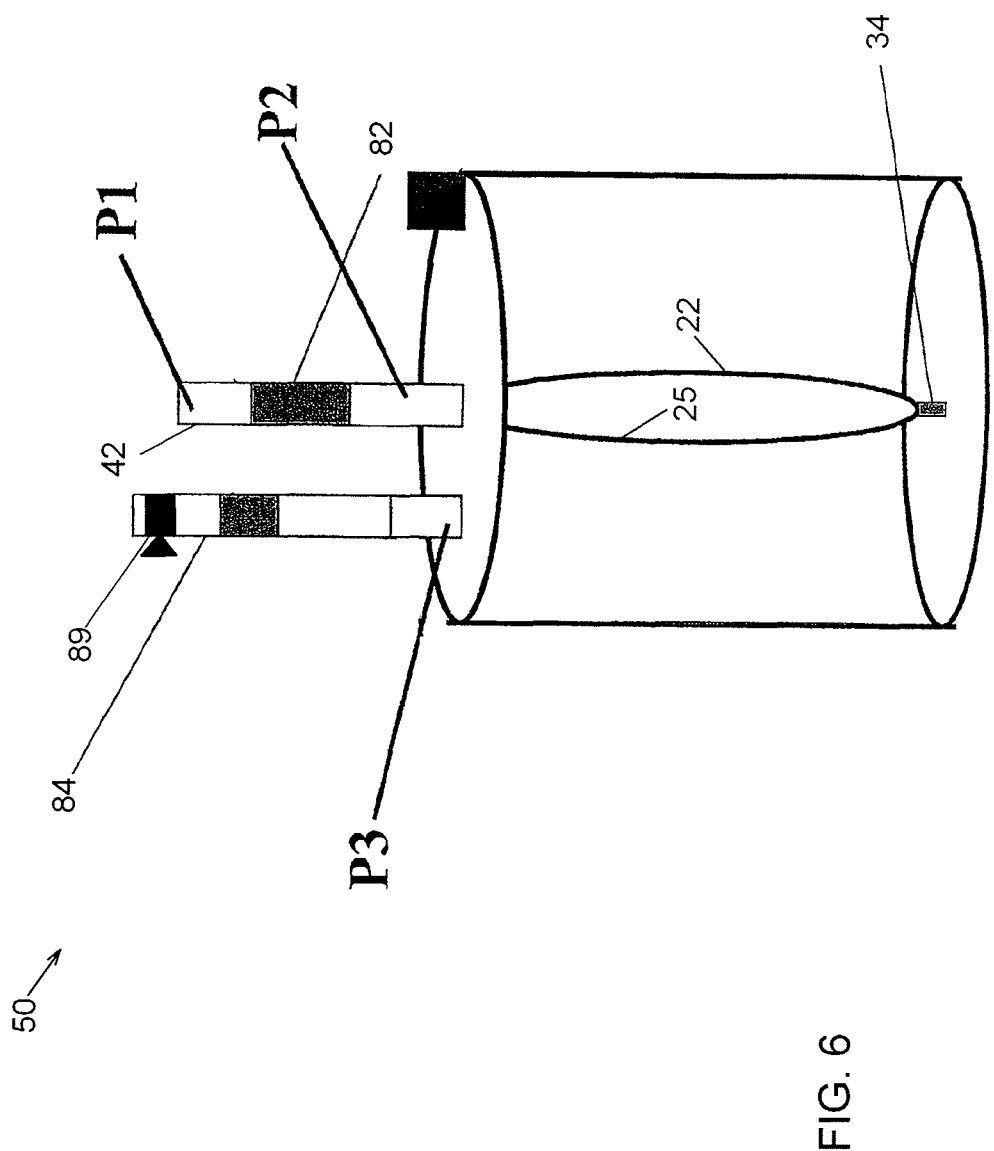
FIG. 6 is a diagram, showing pressure measuring points, of a device according to an embodiment of the invention.

In the embodiment shown in FIG. 6, a particular pressure difference between the pressure (P3) on the patient side 22 of the partition 16 and the pressure (P2) on the actuating side 25 of the partition 16 may be measured and a threshold value may then be used to trigger events that reduce gas inflow from a ventilator 29 to the isolation device 50 by occluding the ventilator path 42, thereby setting the tidal volume and end-inspiratory pressure of the patient. Such a pressure difference may be caused, for example, by a position biaser such as, for example, a tether 34 having two ends, wherein a first one of the ends is connected to the movable partition 16 and a second one of the ends is connected to the housing 13. In addition to creating a pressure difference across the partition, the position biaser may create a restoring force to return the movable partition 16 toward its resting shape and position. In another example, the pressure difference across the movable partition 16, and the restoring force may be generated by an elastic property of the movable partition 16 or its attachments, for example if the movable partition 16 is made from a material comprising an elastic material such as, for example, latex. The pressure difference across the movable partition 16 may be used to control the fresh gas controller 78 or the inlet pressure regulator 82. The pressure difference generated by such a restoring force is generally proportionate to the degree of displacement of the movable partition 16 and is therefore a suitable indicator of tidal volume. A subsequent pressure drop in the ventilator 29 (P1) that accompanies the onset of a ventilator outflow cycle would create a pressure difference across the inlet pressure regulator 82 which may be used to signal reopening of the inlet pressure regulator 82.

Air leaks may occur in the patient or may occur in the airway connections, for example, around an endotracheal tube. Pressure P3 on the patient side 22, while the ventilation path 42 is occluded, may be used to detect and respond to air leaks on the patient side 22 or around the patient connection. When using a re-breathing circuit, air leaks may create a need for compensatory fresh gas flow to prevent loss of pressure on the patient side 22. The pressure P3 on the patient side 22 may be sensed and compared to a desired value. When the pressure P3 is less than the desired value while the ventilation path 42 is occluded, an air leak may be indicated and fresh gas flow may be increased by signaling the fresh gas inflow controller 78. This mechanism creates a new mode of mechanical ventilation, which might best be termed "leak compensated, pressure regulated, volume controlled."

The pressure P3 of the patient side 22 of the partition 16 may be sensed and compared to the pressure P1 of the ventilator 29 to control the timing of occlusion and reopening of the exhaust pathway by way of the exhaust pressure regulator 84, which may comprise, for example a Starling resistor. For example, if the exhaust pressure regulator 84 is in an occluded state, and a transition is measured wherein pressure P3 becomes greater than the pressure P1 after being less than or equal to pressure P1, then a ventilator expiratory cycle may be indicated and an activation signal may be sent to the exhaust pressure regulator 84 to cause the exhaust pressure regulator 84 to open.

Figure 10:
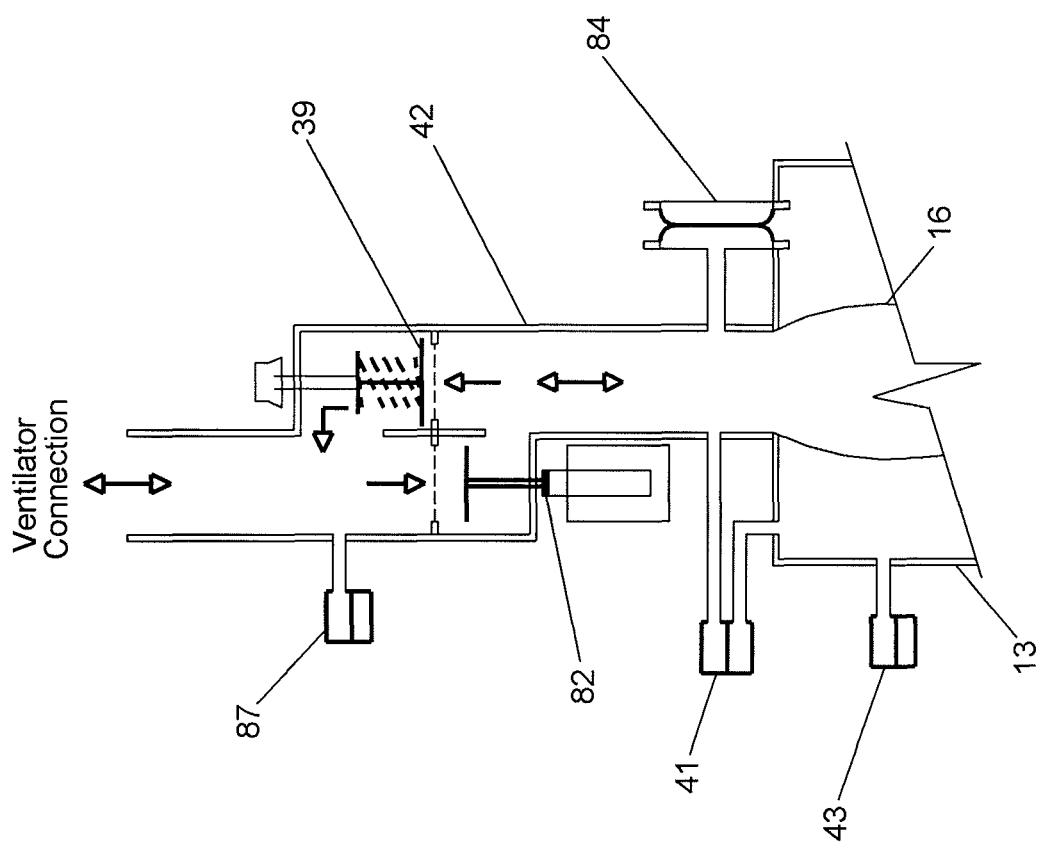
FIG. 10 is a detail of the ventilation path and part of the housing in another embodiment of the invention showing an alternative location for a PEEP valve.

Other functions, including fresh gas inflow and/or ventilator disconnect alarms, may be triggered by pressures P1, P2, and P3 or by the relations of these pressures to one-another. For example, if the pressure of any of P1, P2, or P3 were to remain at 0 psig during a period when the pressure should be above or below 0 psig, then an alarm may sound to indicate that the ventilator may be disconnected or shut off. When using a position biaser 34, a strain gauge may be used to trigger these functions based on tension in a tether of the position biaser 34, rather than on pressure differences. FIG. 10 depicts a ventilation path 42 and housing 13 showing one example of where pressure transducers 87, 43, 41 may be located to measure P1, P3, and the difference between P2 and P3, respectively.

Figure 8:
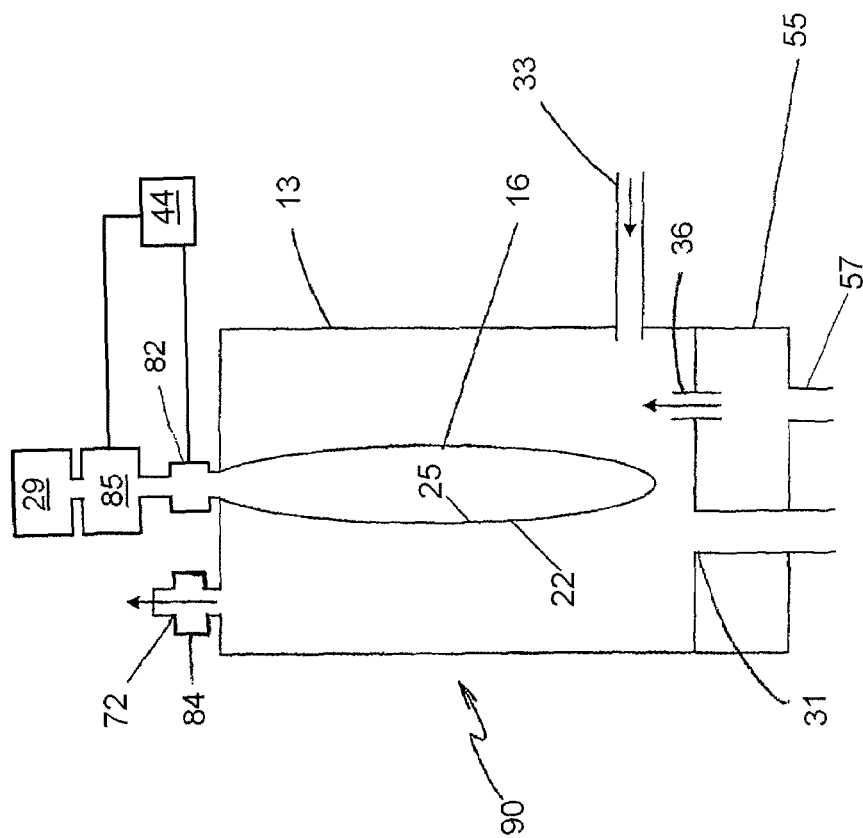
FIG. 8 is a diagram of a device having a pneumotachometer according to another embodiment of the invention.

FIG. 8 depicts an isolation device 90 of the present invention having a pneumotachometer 85. The pneumotachometer 85 may be in pneumatic communication with the actuating side 25 and may be connected between the inlet pressure regulator 82 and the ventilator 29. In such an embodiment, the pneumotachometer 85 may measure the tidal volume during inspiration and the pneumotachometer 85 may cause the inlet pressure regulator 82 to occlude the "path" when a desired tidal volume has been delivered. A controller circuit 44 may be connected to the pneumotachometer 85 and the inlet pressure regulator 82 in order to use a signal from the pneumotachometer 85 to control the regulation of the inlet pressure regulator 82. Pneumotachometers 85 might also be placed between the patient inspiratory orifice 31 and the patient side 22, or between the patient and the $CO_2$ scrubber 55, in the patient exhalation line. Such pneumotachometers 85 may be used to measure patient inspiratory and expiratory tidal volumes. The difference in tidal volume on inspiration and expiration may indicate leaks in the system and/or may be used to control the fresh gas controller 78 to adjust the inflow of fresh gas.

Figure 9:
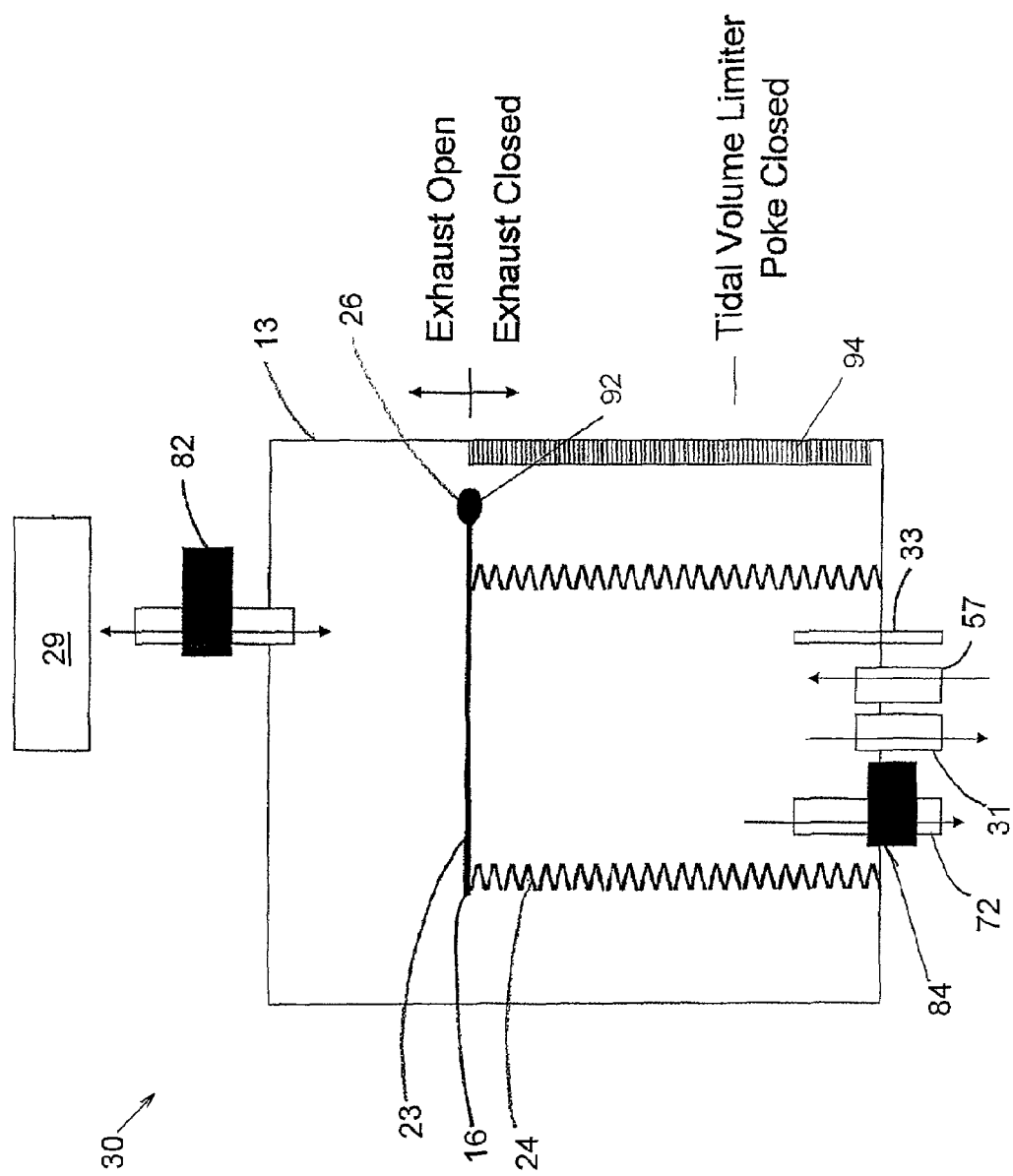
FIG. 9 is a diagram of a device using a bellows according to another embodiment of the invention.

In FIG. 9, yet another embodiment of the invention is depicted. In the isolation device 30 of this embodiment, the movable partition 16 is shown as a diaphragm 23 and a bellows 24. A position indicator 26, which may be disposed on the diaphragm 23, may be used to generate the triggering signals for opening or closing the inlet pressure regulator 82, the exhaust pressure regulator 84, the fresh gas controller 78 for fresh gas inflow, and/or ventilator disconnect alarms. The position indicator 26 may be a strain gauge mounted on the tether or between the movable partition 16 and housing 13. Alternatively, FIG. 9 shows that the position indicator 26 may be an optical or magnetic instrument, which has an emitter 92 attached to the movable partition 16 and a receiver 94 capable of detecting the location of the emitter 92.

Figure 11:
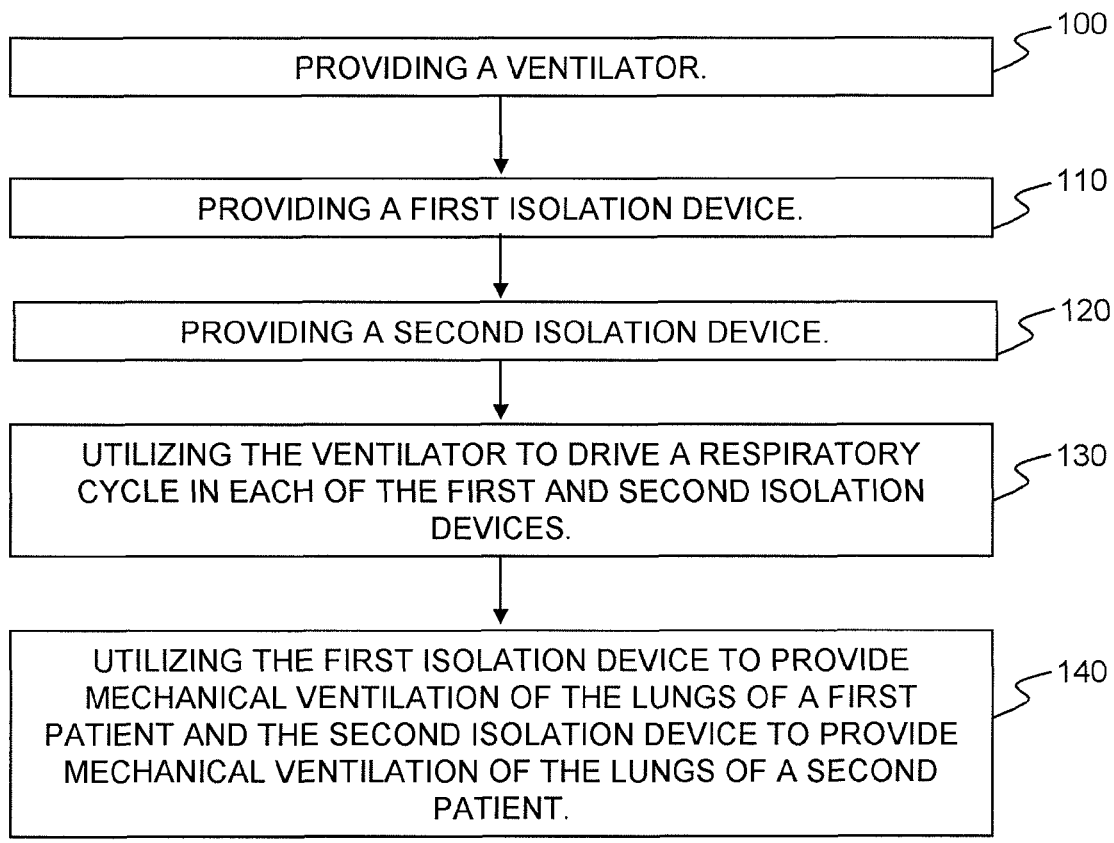
FIG. 11 is a flowchart showing a method according to the invention.

The invention may also be embodied as a method for sharing a single ventilator between at least two patients. FIG. 11 depicts one such method. A method according to the invention may comprise the steps of providing 100 a ventilator, providing 110 a first isolation device, providing 120 a second isolation device, utilizing 130 the ventilator to drive a respiratory cycle in each of the first and second isolation devices, and utilizing 140 the first isolation device to provide mechanical ventilation of the lungs of a first patient and the second isolation device to provide mechanical ventilation of the lungs of a second patient. The first and second isolation devices may be of many types known in the art, for example, the type disclosed in the '799 patent, or the type described above. The first and second isolation devices each may or may not be equipped with an inlet pressure regulator and/or and exhaust pressure regulator. The inlet and/or exhaust pressure regulators may be used to modify the delivery conditions, for example, pressure and volume, of gas delivered to patients' lungs for mechanical ventilation, from the conditions of gas delivered from the ventilator to drive the respiratory cycle.

Figure 12:
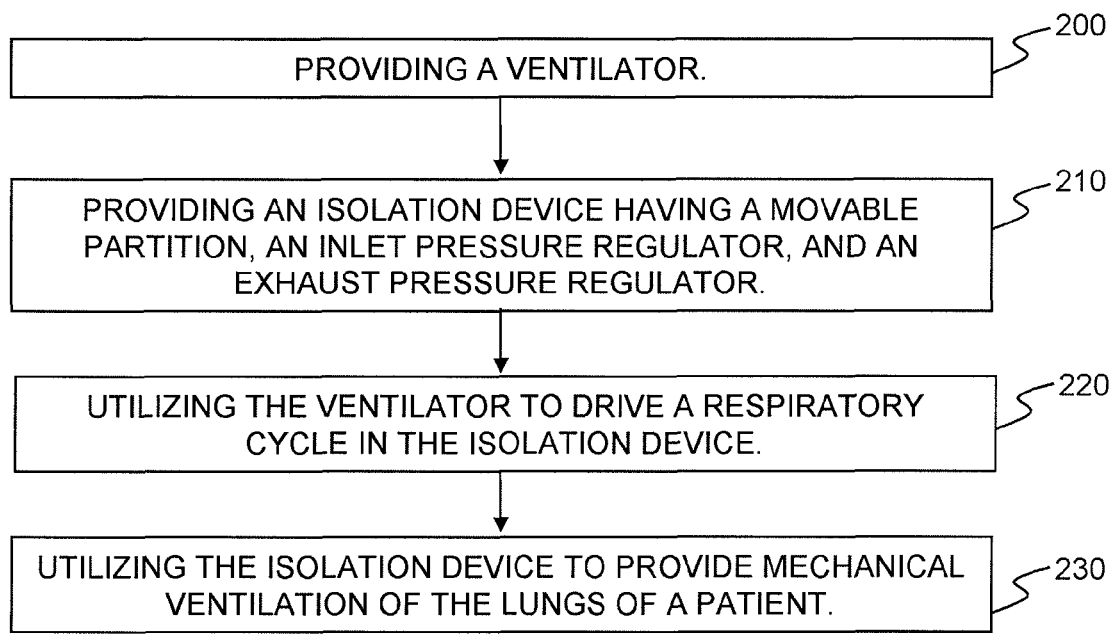
FIG. 12 is a flowchart showing a method according to another embodiment of the invention.

FIG. 12 depicts a method for altering the performance characteristics of a ventilator that is in keeping with an embodiment of the invention. A method according to the invention may comprise the steps of providing 200 a ventilator, providing 210 an isolation device that includes an inlet pressure regulator and an exhaust pressure regulator, utilizing 220 the ventilator to drive the isolation device, utilizing 230 the isolation device to provide mechanical ventilation of the lungs of a patient. The inlet pressure regulator and/or the exhaust pressure regulator may modify the delivery conditions, for example, pressure and volume, of gas delivered to the patient's lungs for mechanical ventilation, from the properties of gas delivered from the ventilator to drive the respiratory cycle.

It will now be recognized that the invention provides a system and method by which a single ventilator may be used to aseptically ventilate one or more patients. Further, it will be recognized that less-expensive ventilators may be used to ventilate one or more patients by providing isolation devices which can individually regulate tidal volume, oxygen fraction, and PEEP. The system is also able to isolate the ventilator from an infected patient, and to reduce the hazard of contagion for respiratory therapists who clean and re-deploy ventilators. This system also may allow for reduction of the amount of oxygen used, which may be helpful when oxygen is in short supply, for example during a mass casualty event.

Although the present invention has been described with respect to one or more particular embodiments, it will be understood that other embodiments of the present invention may be made without departing from the spirit and scope of the present invention.

What is claimed is:

1. A ventilator sharing system, comprising:
    a ventilator;
    at least two isolation devices for delivering gas to at least two patients and preventing gas from the patients from reaching the ventilator, wherein each isolation devices is in pneumatic communication with the ventilator.

2. The ventilator sharing system of claim 1, wherein each of the at least two isolation devices further comprise:
    a movable partition having a patient side on a first side of the partition and an actuating side on a second side of the partition; and
    a housing disposed about the movable partition, wherein the housing has an inlet connected to the ventilator, and wherein the inlet is in fluid communication with the actuating side of the movable partition.

3. The ventilator sharing system of claim 2, wherein each of the at least two isolation devices further comprise:
    an inlet pressure regulator in fluid communication with the actuating side of the movable partition; and
    an exhaust pressure regulator for controlling a positive-end-of-expiration pressure ("PEEP") in fluid communication with the patient side of the movable partition.

4. The ventilator sharing system of claim 3, wherein at least one of the isolation devices further comprises a $CO_2$ scrubber in fluid communication with the patients side of the movable partition.

5. The ventilator sharing system of claim 3, wherein the movable partition is a flexible bag.

6. The ventilator sharing system of claim 3, wherein the movable partition is comprised of an elastic material.

7. The ventilator sharing system of claim 3, wherein the movable partition comprises a bellows and a diaphragm.

8. The ventilator sharing system of claim 3, wherein at least one of the isolation devices further comprises a position sensor capable of detecting a position of the movable partition.

9. The ventilator sharing system of claim 3, further comprising a pneumotachometer for measuring a gas volume of breathing-gas, the pneumotachometer being connected between the inlet and the ventilator.

10. The ventilator sharing system of claim 9, further comprising a controller circuit, wherein the controller circuit is in communication with the pneumotachometer, and the controller circuit is in communication with the inlet pressure regulator, and wherein the controller circuit is capable of using a gas volume measurement of the pneumotachometer to control a pressure limiting characteristic of the inlet pressure regulator.

11. The ventilator sharing system of claim 10, wherein the inlet pressure regulator comprises:
    a flexible tube connected between the pneumotachometer and the inlet;
    a caliper capable of variably occluding the flexible tube; and
    wherein the controller circuit is capable of using a gas volume measurement of the pneumotachometer to control the extent of occlusion of the flexible tube by the caliper.

12. The ventilator sharing system of claim 3, wherein the housing has an orifice for receiving fresh gas from a fresh gas source, and wherein the orifice is in fluid communication with the patient side of the movable partition.

13. The ventilator sharing system of claim 3, further comprising an exhaust line extending from the patient side of the housing.

14. The ventilator sharing system of claim 3, wherein the inlet pressure regulator comprises a flexible tube and a caliper.

15. The ventilator sharing system of claim 3, wherein the exhaust pressure regulator comprises a flexible tube and a caliper.

16. The ventilator sharing system of claim 3, wherein the exhaust pressure regulator comprises a Starling resistor.

17. The ventilator sharing system of claim 3, wherein at least one of the isolation devices further comprises a tether having a first end and a second end, wherein the first end is connected to the movable partition and the second end is connected to the housing.

18. The ventilator sharing system of claim 3, wherein at least one of the isolation devices further comprises an adjustable PEEP valve.

19. The ventilator sharing system of claim 3, wherein the housing of at least one of the isolation devices further comprises a patient orifice in fluid communication with the patient side of the movable partition and the patient orifice is adaptable to be in fluid communication with a patient.

20. The ventilator sharing system of claim 19, wherein at least one of the isolation devices further comprises a pneumotachometer connected to the patient orifice and capable of measuring a gas volume of gas flowing into and/or out of the housing.

* * * * *